US012281182B2

(12) United States Patent
Kolesa et al.

(10) Patent No.: US 12,281,182 B2
(45) Date of Patent: Apr. 22, 2025

(54) SOLID STATE FORMS OF VOCLOSPORIN

(71) Applicant: TEVA PHARMACEUTICALS INTERNATIONAL GMBH, Jona (CH)

(72) Inventors: Pavel Kolesa, Hlubocec (CZ); Ladislav Cvak, Opava-Zlatniky (CZ); Alexandr Jegorov, Dobra Voda (CZ); Katerina Ondruszova, Ostrava (CZ)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 124 days.

(21) Appl. No.: 18/100,032

(22) Filed: Jan. 23, 2023

(65) Prior Publication Data
US 2023/0167156 A1 Jun. 1, 2023

Related U.S. Application Data

(63) Continuation of application No. 17/286,542, filed as application No. PCT/US2019/057122 on Oct. 21, 2019, now Pat. No. 11,584,779.

(60) Provisional application No. 62/856,224, filed on Jun. 3, 2019, provisional application No. 62/747,701, filed on Oct. 19, 2018.

(51) Int. Cl.
*C07K 7/64* (2006.01)
(52) U.S. Cl.
CPC .......... *C07K 7/645* (2013.01); *C07B 2200/13* (2013.01)

(58) Field of Classification Search
None
See application file for complete search history.

(56) References Cited

U.S. PATENT DOCUMENTS 6,998,385 B2 2/2006 Naicker et al.

FOREIGN PATENT DOCUMENTS

WO 2006014872 A2 2/2006

OTHER PUBLICATIONS

Maeng, Jun-Ho, et al., "Organozirconium Chemistry on Cyclosporin: A Novel Process for the Highly Stereoselective Synthesis of (E)ISA247 (Voclosporin) and Close Analogues", Synthesis (2012) vol. 44, pp. 63-68.
International Search Report and Written Opinion of the International Searching Authority issued in corresponding application PCT/US2019/057122 mailed Apr. 14, 2020 (19 pages).
Isaac John Khan, "The Utility of L-Tyrosine Based Polycarbonate Copolymers Containing Poly(Ethylene Glycol) as a Degradable Carrier for the Release of a Hydrophobic Peptide Molecule", A dissertation submitted to the Graduate School-New Brunswick Rutgers, the State University of New Jersey and The Graduate School of Biomedical Sciences University of Medicine and Dentistry of New Jersey, Oct. 2009.
Schultz, Clyde "Voclosporin as a Treatment for Noninfectious Uveitis", Ophthalmology and Eye Diseases vol. 5 (2013) pp. 5-10.

*Primary Examiner* — Sergio Coffa
(74) *Attorney, Agent, or Firm* — Carter, DeLuca & Farrell LLP

(57) ABSTRACT

The present disclosure relates to solid state forms of Voclosporin and salts thereof, processes for preparation thereof and pharmaceutical compositions thereof.

9 Claims, 9 Drawing Sheets

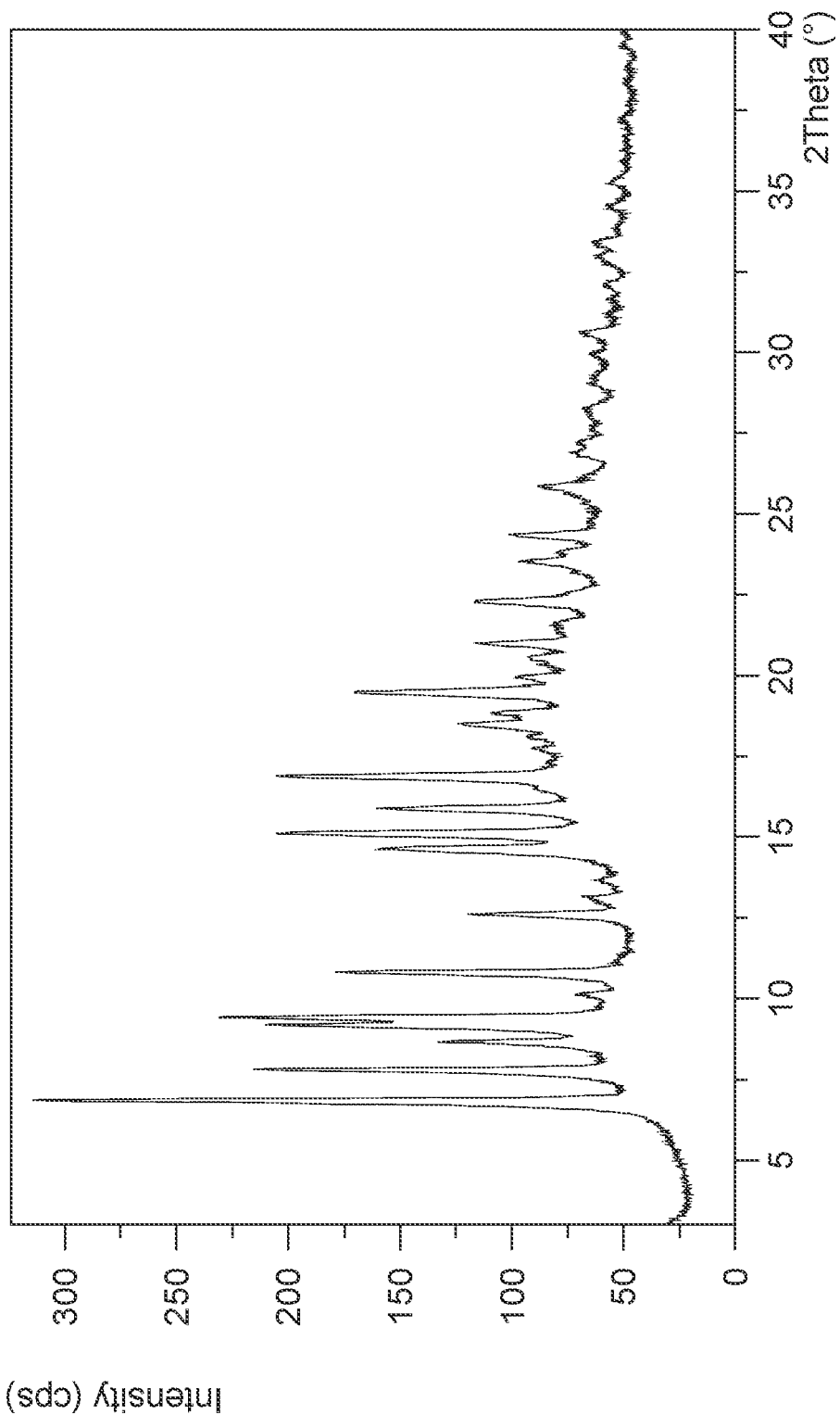
Figure 1. PXRD pattern of Voclosporin form A

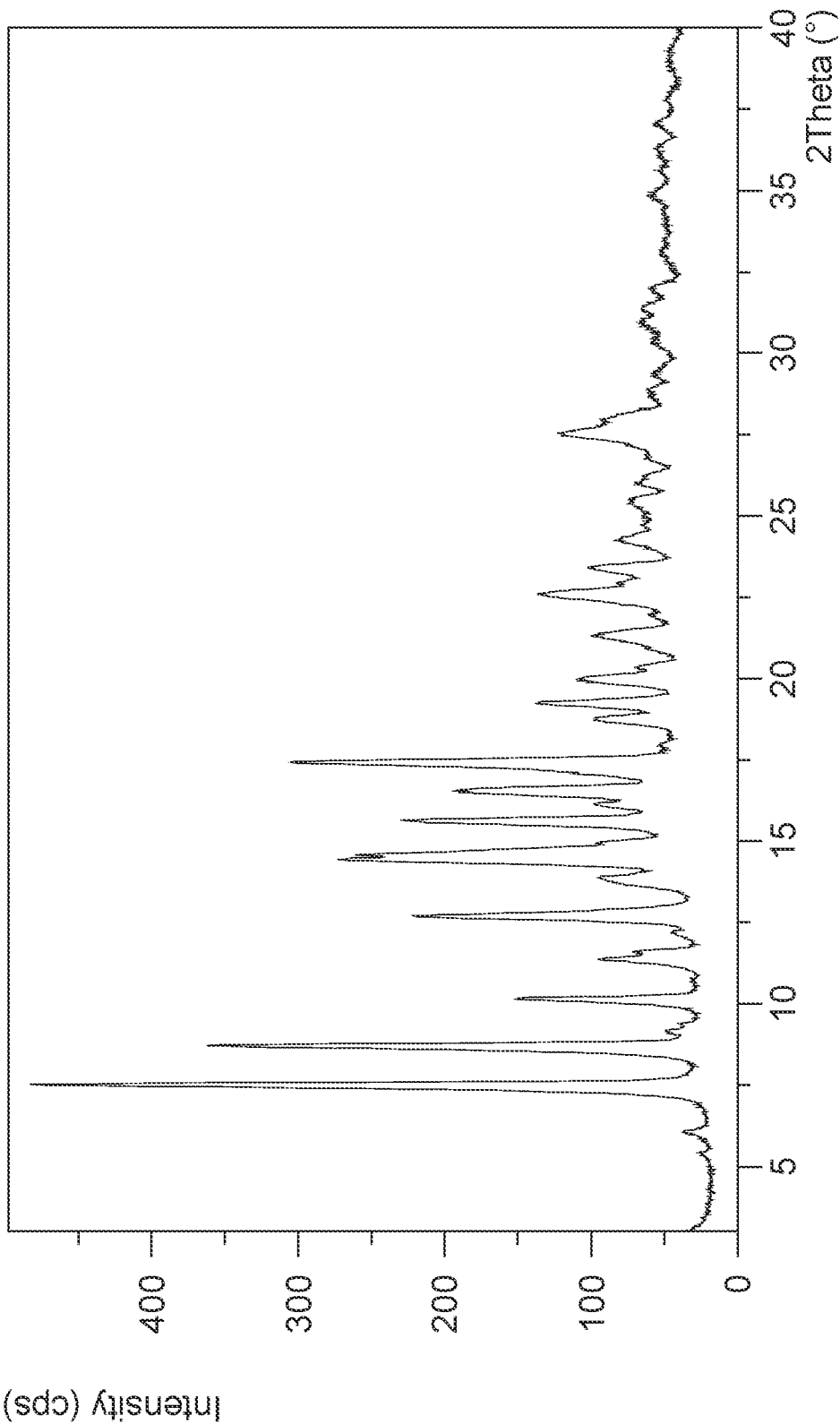
Figure 2. PXRD pattern of Voclosporin form B

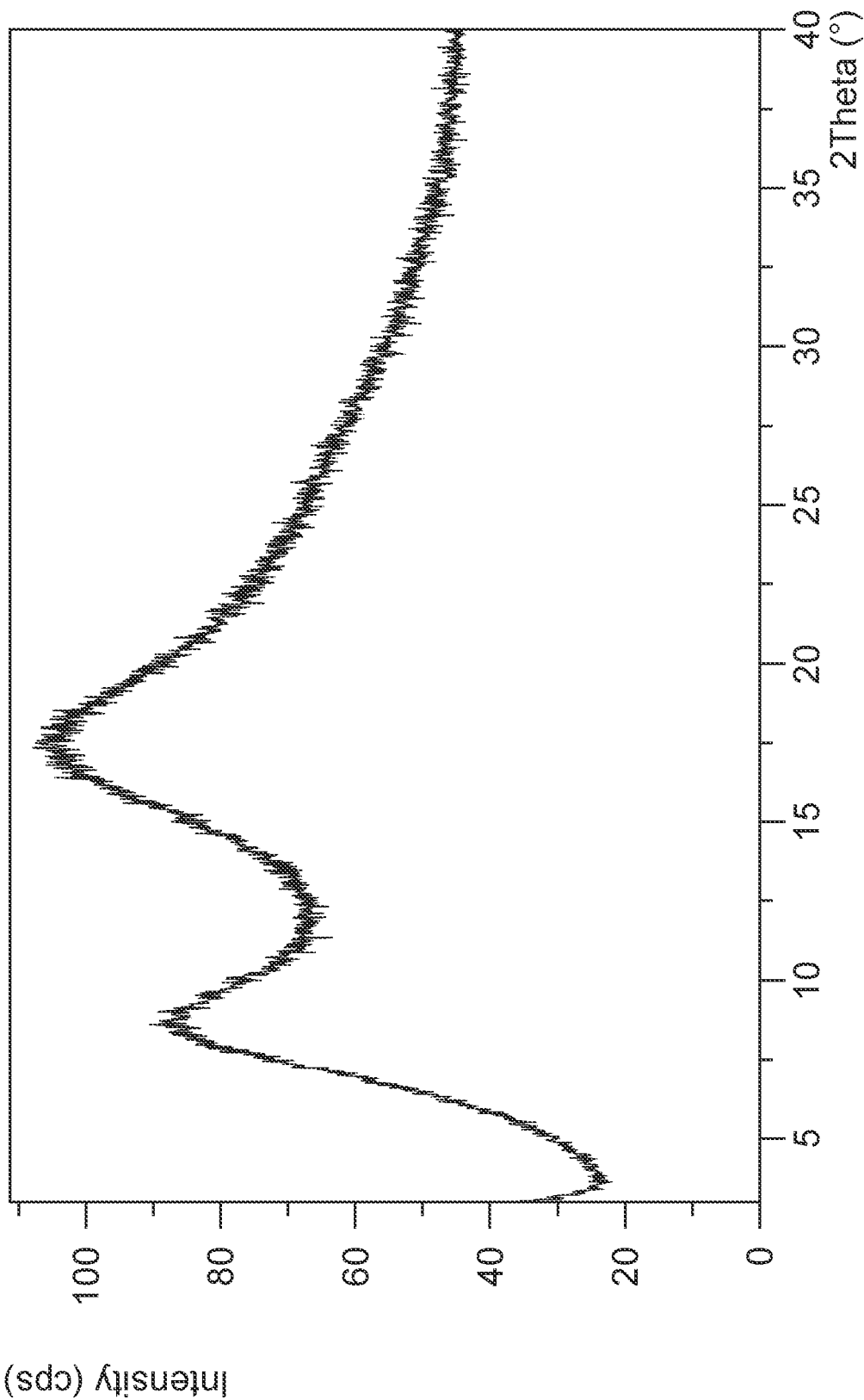
Figure 3: PXRD pattern of Amorphous Voclosporin

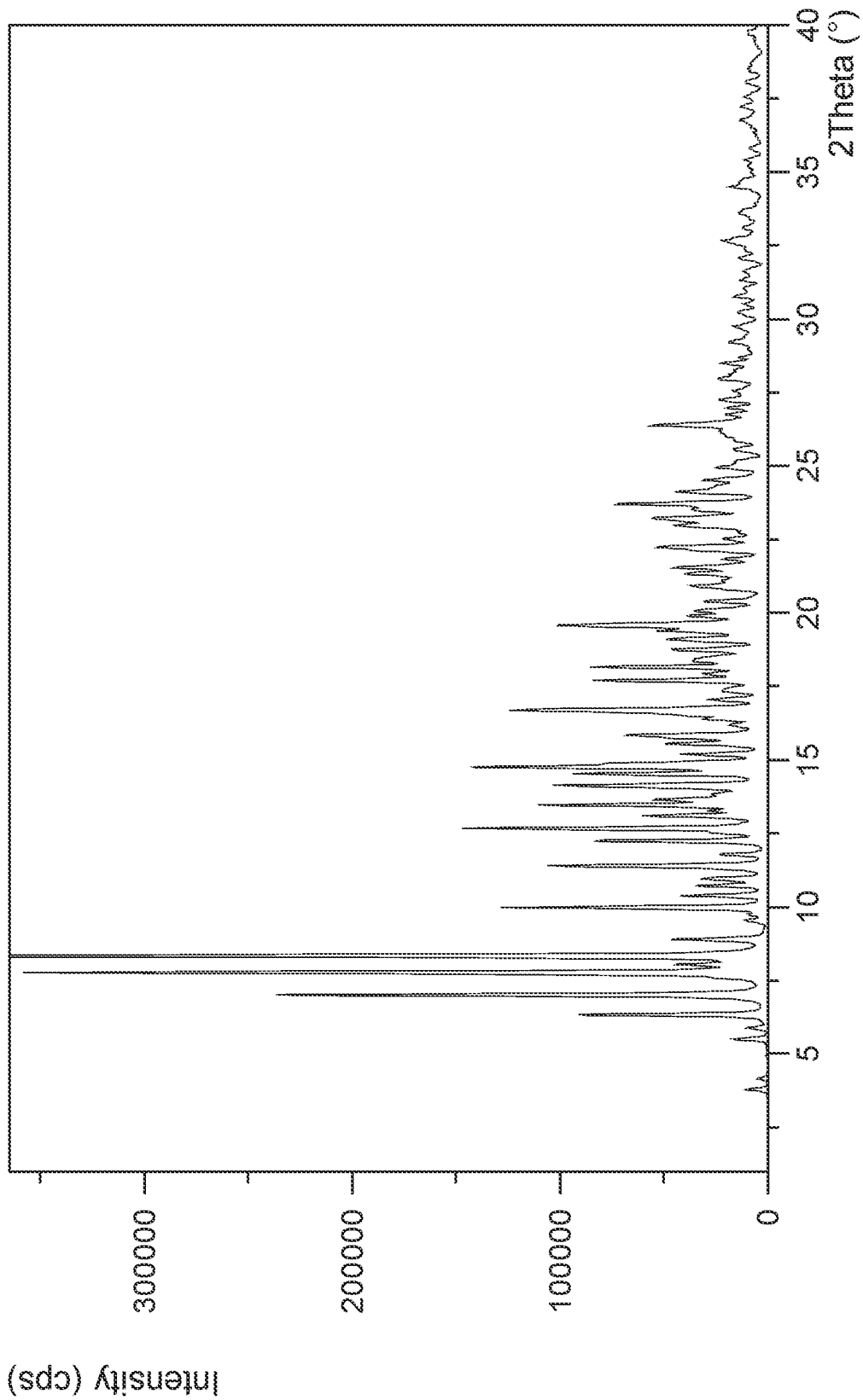
Figure 4. PXRD pattern of Voclosporin form C

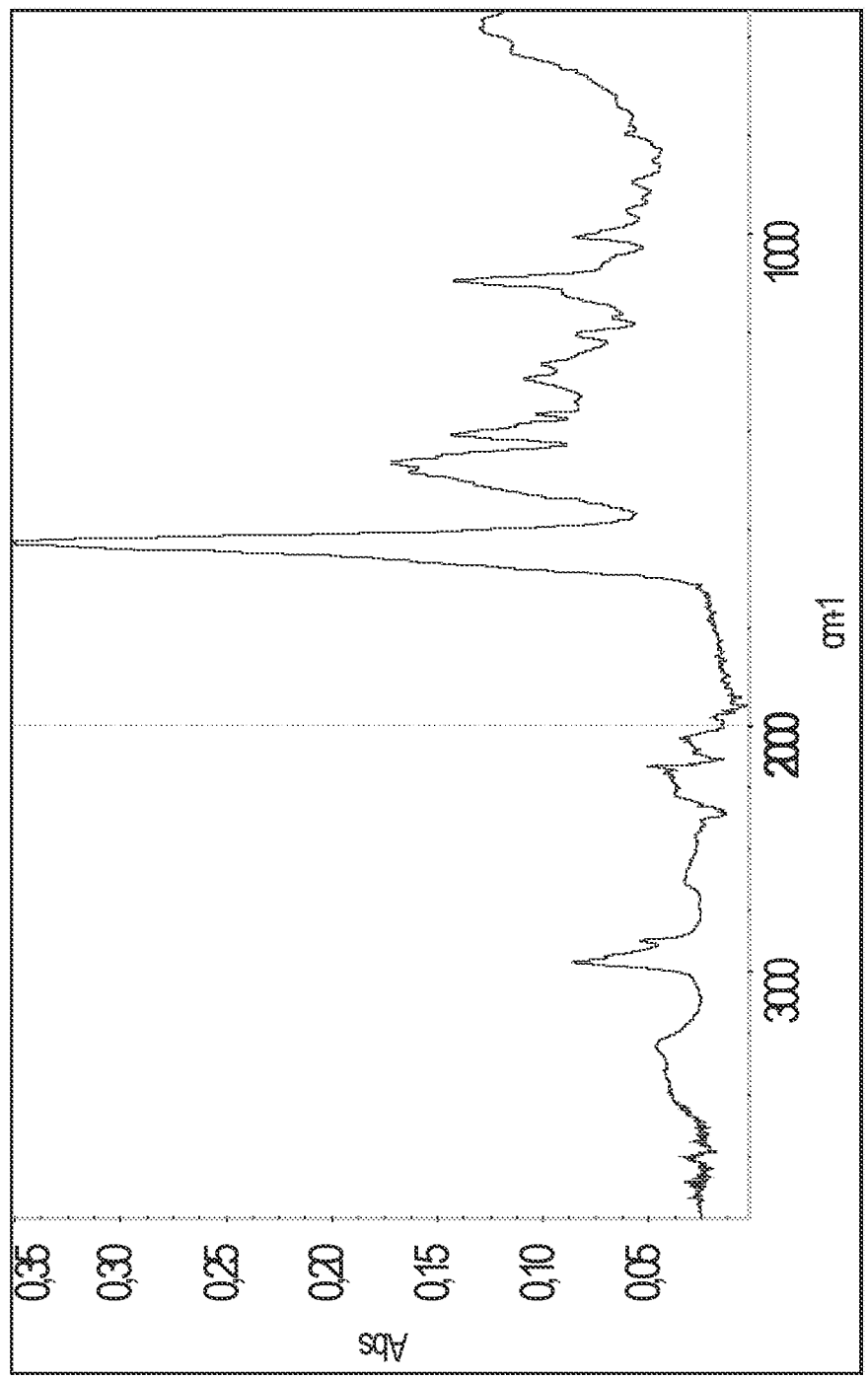
Figure 5. FT-IR spectrum of Voclosporin form B

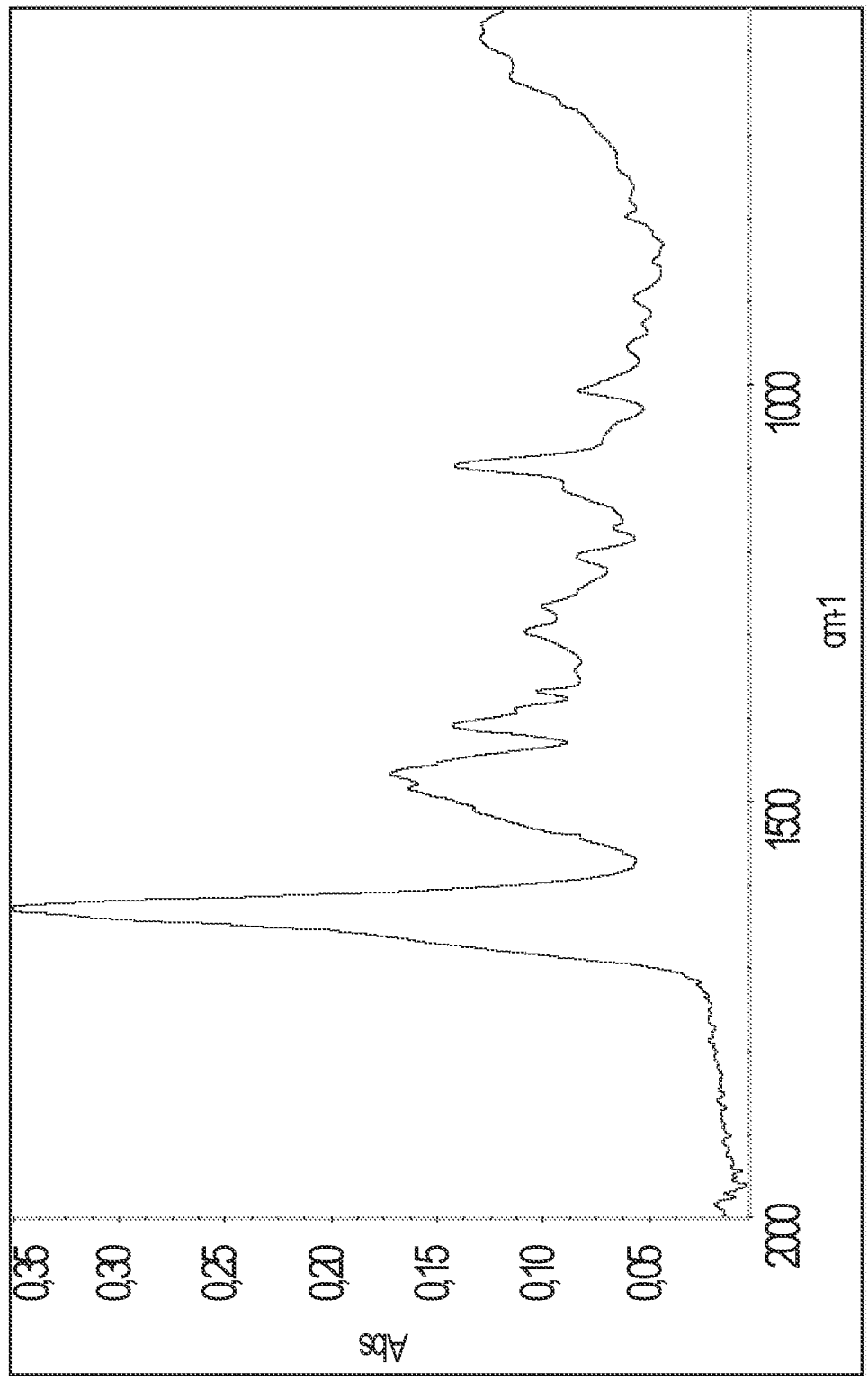
Figure 6. Zoomed FT-IR spectrum of Voclosporin form B

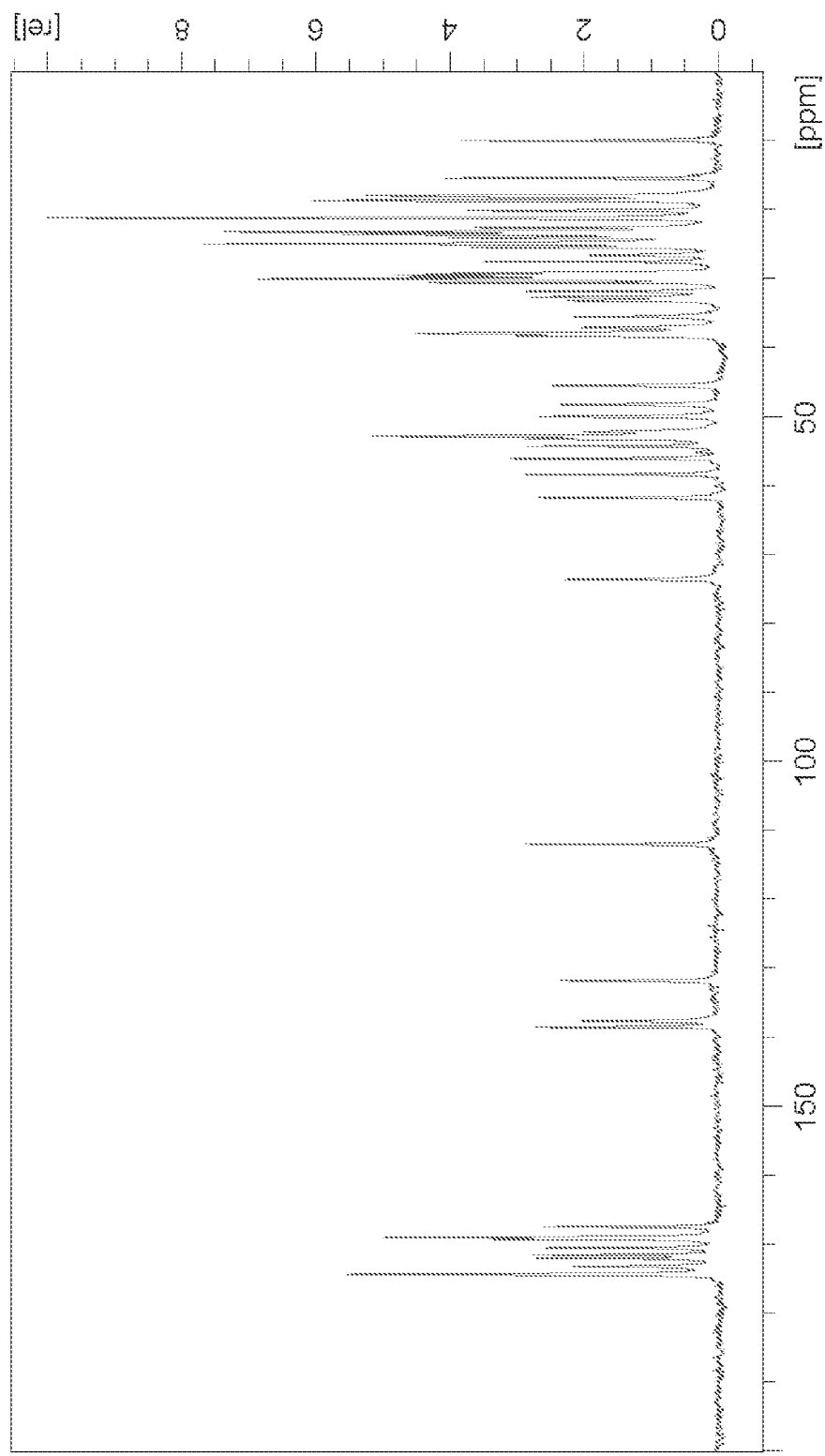
Figure 7. 13C solid state NMR spectrum (range from 200-0 ppm) of Form B

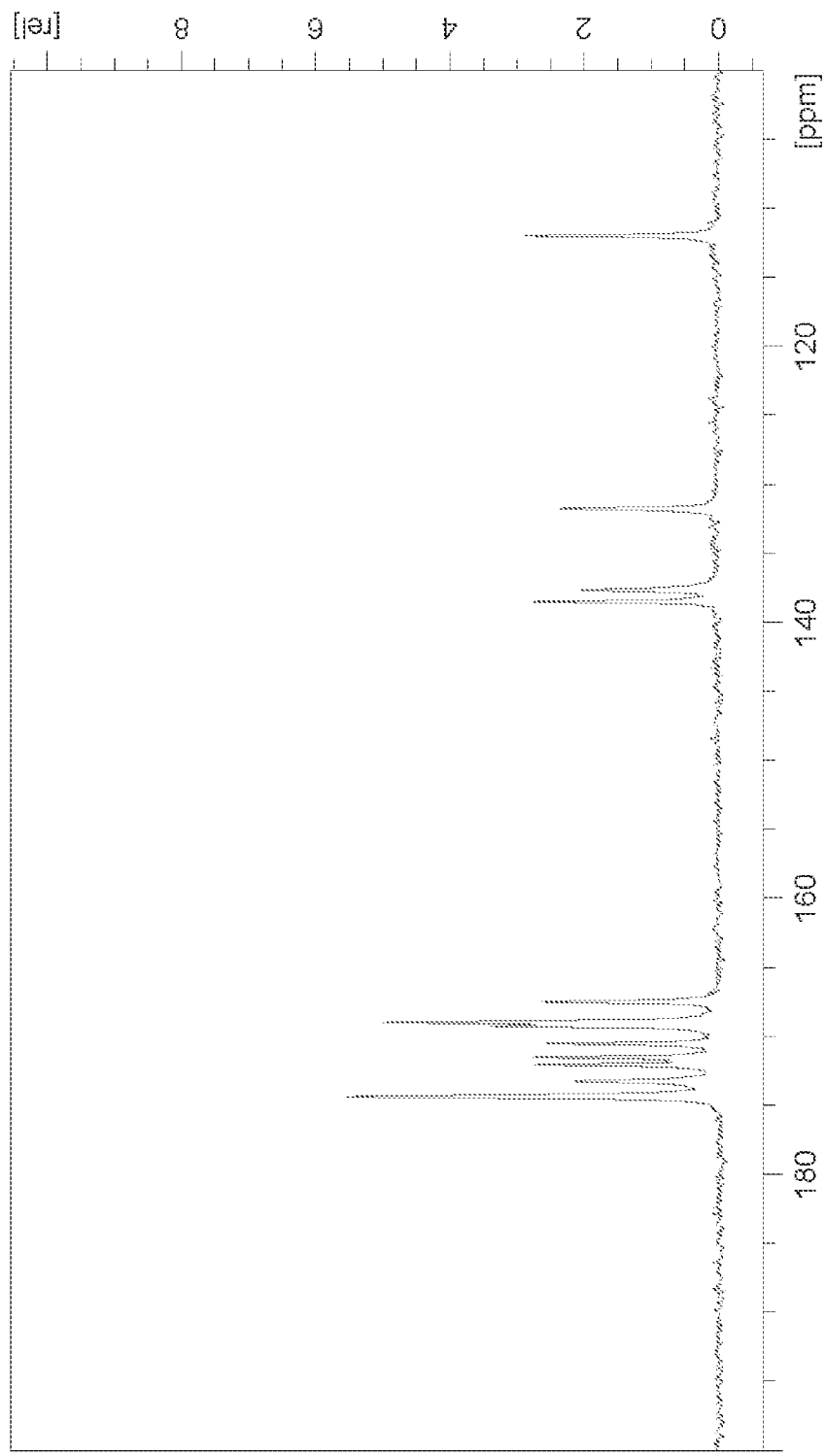
Figure 8. 13C solid state NMR spectrum (range from 200-100 ppm) of Form B

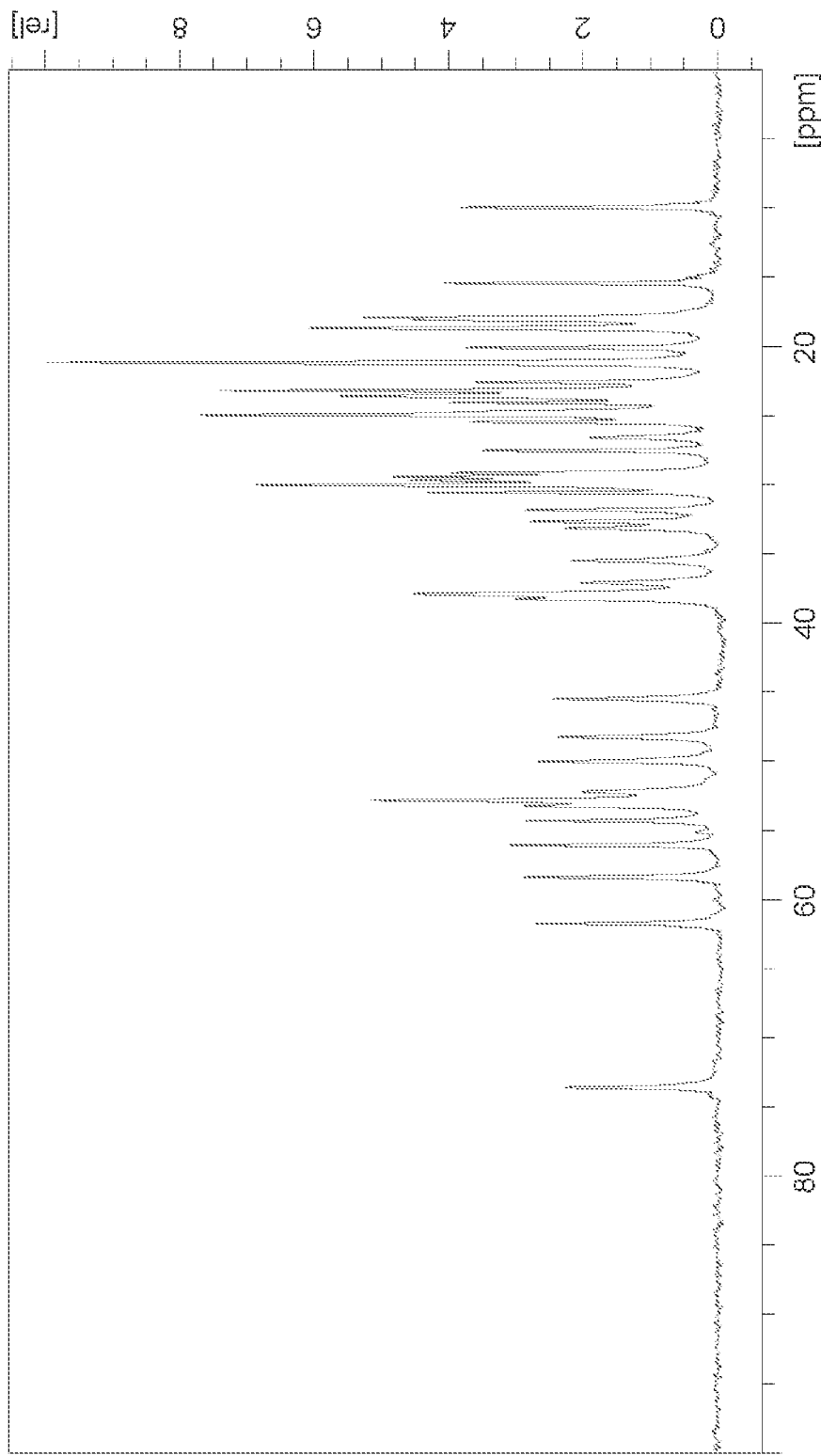
Figure 9. 13C solid state NMR spectrum (range from 100-0 ppm) of Form B

SOLID STATE FORMS OF VOCLOSPORIN

CROSS REFERENCE TO RELATED APPLICATIONS

This application is a Continuation of U.S. application Ser. No. 17/286,542, filed Apr. 19, 2021, which is a National Stage of, and claims priority to and the benefit of, International Patent Application No. PCT/US2019/057122 filed Oct. 21, 2019, which, in turn, claims the benefit of and priority to, U.S. Provisional Patent Application No. 62/747,701, filed Oct. 19, 2018, and U.S. Provisional Patent Application No. 62/856,224, filed Jun. 3, 2019, the entire disclosures of each of which are incorporated by reference herein.

TECHNICAL FIELD

The present disclosure relates to solid state forms of Voclosporin and salts thereof, processes for preparation thereof and pharmaceutical compositions thereof.

BACKGROUND

Voclosporin is a structural analog of cyclosporine A, with an additional single carbon extension that has a double-bond on one side chain. Voclosporin has the chemical name (3S,6S,9S,12R,15S,18S,21S,24S,30S,33S)-30-Ethyl-33-[(1R,2R,4E)-1-hydroxy-2-methyl-4,6-heptadien-1-yl]-6,9,18,24-tetraisobutyl-3,21-diisopropyl-1,4,7,10,12, 15, 19,25, 28-nonamethyl-1,4,7,10,13,16,19,22,25,28,31-undecaazacyclotritriacontane-2,5,8, 11, 14, 17,20,23,26,29,32-undecone and the following chemical structure:

Voclosporin is reported to be a semisynthetic structural analogue of cyclosporine that exerts its immunosuppressant effects by inhibition of the calcineurin signal-transduction pathway and is in Phase 3 Clinical Development for Lupus Nephritis.

Voclosporin and process for preparation thereof are known from International Patent Application No. WO 1999/18120.

Certain mixtures of cis and trans-isomers of cyclosporin A analogs referred to as ISATx247 in different ratios are known from U.S. Pat. Nos. 6,998,385, 7,332,472 and 9,765,119.

Polymorphism, the occurrence of different crystal forms, is a property of some molecules and molecular complexes. A single compound, like Voclosporin, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for solid state forms (including solvated forms) of Voclosporin and salts thereof.

SUMMARY

The present disclosure relates to solid state forms of Voclosporin and salts thereof, to processes for preparation thereof, and to pharmaceutical compositions comprising these solid state forms.

The present disclosure also provides uses of the solid state forms of Voclosporin and salts thereof for preparing other solid state forms of Voclosporin, Voclosporin salts and solid state forms thereof.

In another embodiment, the present disclosure encompasses the above described solid state forms of Voclosporin and salts thereof for use in the preparation of pharmaceutical compositions and/or formulations, preferably for the treatment of lupus nephritis.

In another embodiment the present disclosure encompasses the use of the above described solid state form of Voclosporin and salts thereof for the preparation of pharmaceutical compositions and/or formulations.

The present disclosure further provides pharmaceutical compositions comprising the solid state forms of Voclosporin and salts thereof according to the present disclosure.

In yet another embodiment, the present disclosure encompasses pharmaceutical formulations comprising the above described solid state forms of Voclosporin and salts thereof and at least one pharmaceutically acceptable excipient, preferably for oral administration in a dosage forms such as tablets, capsules etc.

The present disclosure encompasses processes to prepare said pharmaceutical formulations of Voclosporin comprising combining the above solid state forms and at least one pharmaceutically acceptable excipient.

The solid state forms as defined herein, as well as the pharmaceutical compositions or formulations of the solid state form of Voclosporin and salts thereof, can be used as medicaments, particularly for the treatment of lupus nephritis.

The present disclosure also provides methods of treating lupus nephritis, comprising administering a therapeutically effective amount of the solid state form of Voclosporin and salts thereof of the present disclosure, or at least one of the above pharmaceutical compositions or formulations, to a subject suffering from lupus nephritis, or otherwise in need of the treatment.

The present disclosure also provides uses of the solid state forms of Voclosporin and salts thereof of the present disclosure, or at least one of the above pharmaceutical compositions or formulations for the manufacture of a medicament for treating lupus nephritis.

BRIEF DESCRIPTION OF THE DRAWINGS

FIG. 1 shows a powder X-ray diffraction pattern ("powder XRD" or "PXRD") of Voclosporin form A.

FIG. 2 shows a PXRD of Voclosporin form B.

FIG. 3 shows a PXRD of Amorphous Voclosporin.

FIG. 4 shows a PXRD of Voclosporin form C.

FIG. 5 shows an FT-IR spectrum of Voclosporin form B.

FIG. 6 shows a zoomed FT-IR spectrum of Form B.

FIG. 7 shows a $^{13}$C solid state NMR spectrum (range from 200-0 ppm) of Form B.

FIG. 8 shows a $^{13}$C solid state NMR spectrum (range from 200-100 ppm) of Form B.

FIG. 9 shows a $^{13}$C solid state NMR spectrum (range from 100-0 ppm) of Form B.

DETAILED DESCRIPTION

The present disclosure relates to solid state forms of Voclosporin and salts thereof, processes for preparation thereof and pharmaceutical compositions comprising said solid state forms.

The solid state forms of Voclosporin according to the present disclosure may have advantageous properties selected from at least one of: chemical or polymorphic purity, flowability, solubility, dissolution rate, bioavailability, morphology or crystal habit, stability-such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Voclosporin and salts thereof referred to herein as being characterized by graphical data "as depicted in" a Figure will thus be understood to include any crystal forms of the Voclosporin and salts thereof, characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by PXRD. Thus, solid state of Voclosporin and Voclosporin salts, described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state form of Voclosporin and Voclosporin salts. Accordingly, in some embodiments of the disclosure, the described solid state forms of Voclosporin and Voclosporin salts may contain from about 1% to about 20% (w/w), from about 5% to about 20% (w/w), or from about 5% to about 10% (w/w) of one or more other solid state forms of the same Voclosporin and Voclosporin salts.

As used herein, unless stated otherwise, PXRD peaks reported herein are preferably measured using CuK$_\alpha$ radiation, λ=1.5418 Å.

As used herein, percentages are wt % unless otherwise indicated.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based upon the volume of that mixture. For example, adding MTBE (1.5 v/v) to a 100 ml reaction mixture would indicate that 150 mL of MTBE was added.

As used herein, the term "reduced pressure" refers to a pressure of about 10 mbar to about 50 mbar.

The present disclosure includes a crystalline form of Voclosporin designated as form A. The crystalline form A of Voclosporin can be characterized by data selected from one or more of the following: a PXRD pattern having peaks at 6.9, 7.8, 10.8, 15.1 and 16.9 degrees 2-theta±0.2 degrees 2-theta; a PXRD pattern as depicted in FIG. 1 and combinations of these data.

Crystalline form A of Voclosporin may be further characterized by the PXRD pattern having peaks at 6.9, 7.8, 10.8, 15.1 and 16.9 degrees 2-theta±0.2 degrees 2-theta, and also having one, two, three, four or five additional peaks at 9.2, 9.4, 12.6, 15.9 and 19.5 degrees 2-theta±0.2 degrees 2-theta.

Crystalline form A of Voclosporin may be characterized by each of the above characteristics alone/or by all possible combinations, e.g., by PXRD pattern having peaks at 6.9, 7.8, 10.8, 15.1 and 16.9 degrees 2-theta±0.2 degrees 2-theta and a PXRD pattern as depicted in FIG. 1.

Crystalline form A of Voclosporin may alternatively or additionally be characeterised by a PXRD pattern having peaks at 6.9, 7.8, 9.2, 9.4, 10.8, 12.6, 15.1, 15.9, 16.9 and 19.5 degrees 2-theta±0.2 degrees 2-theta.

The present disclosure includes a crystalline form of Voclosporin designated as form B. The crystalline form B of Voclosporin can be characterized by data selected from one or more of the following: a PXRD pattern having peaks at 7.5, 11.4, 15.6, 16.6 and 17.4 degrees 2-theta±0.2 degrees 2-theta; a PXRD pattern as depicted in FIG. 2; a solid state $^{13}$C NMR spectrum having characteristic peaks at 174.3, 170.5, 167.5, 138.5 and 131.7 ppm±0.2 ppm; a solid state $^{13}$C NMR spectrum having the following chemical shift absolute differences from reference peak at 111.9 ppm±1 ppm: 62.4, 58.5, 55.5, 26.5 and 19.8 ppm±0.1 ppm; a solid state $^{13}$C NMR spectrum substantially as depicted in FIGS. 7, 8 and/or 9; an FT-IR spectrum having a full peak list of: 583, 797, 896, 953, 1007, 1097, 1172, 1206, 1266, 1296, 1368, 1409, 1467, 1485, 1628, 2162, 2874 and 2961 cm$^{-1}$±4 cm$^{-1}$; and combinations of these data.

Crystalline form B of Voclosporin may be alternatively or additionally characterized by the PXRD pattern having peaks at 7.5, 11.4, 15.6, 16.6 and 17.4 degrees 2-theta±0.2 degrees 2-theta, and also having one, two, three, four or five additional peaks at 6.1, 8.7, 14.5, 18.7 and 19.3 degrees 2-theta±0.2 degrees 2-theta. and combinations of these data.

Crystalline Form B of Voclosporin may alternatively or additionally be characterized by a solid state $^{13}$C NMR spectrum having the following full peak list of: 174.3, 173.2, 172.0, 171.5, 170.5, 169.2, 169.0, 167.5, 138.5, 137.6, 131.7, 111.9, 73.6, 61.7, 58.3, 56.0, 54.3, 53.2, 52.8, 52.2, 50.0, 48.2, 45.5, 38.2, 37.9, 37.1, 35.5, 33.1, 32.6, 31.8, 30.5, 30.3, 30.0, 29.7, 29.4, 29.1, 27.5, 26.6, 25.4, 24.9, 24.0, 23.6, 23.2, 22.5, 21.1, 20.1, 18.7, 18.0, 17.9, 15.4 and 9.9 ppm±0.2 ppm.

Crystalline form B of Voclosporin may be characterized by each of the above characteristics alone/or by all possible combinations, e.g., by PXRD pattern having peaks at 7.5, 11.4, 15.6, 16.6 and 17.4 degrees 2-theta±0.2 degrees 2-theta and a PXRD pattern as depicted in FIG. 2.

Crystalline form B of Voclosporin may alternatively or additionally be characerised by a PXRD pattern having peaks at 6.1, 7.5, 8.7, 11.4, 14.5, 15.6, 16.6, 17.4, 18.7 and 19.3 degrees 2-theta±0.2 degrees 2-theta.

The present disclosure includes an Amorphous Voclosporin; Amorphous Voclosporin may be characterized by a PXRD pattern as depicted in FIG. 3.

The present disclosure includes a crystalline form of Voclosporin designated as form C. The crystalline form C of Voclosporin can be characterized by data selected from one or more of the following: a PXRD pattern having peaks at 6.3, 7.0, 8.3, 12.2 and 14.1 degrees 2-theta±0.2 degrees 2-theta; a PXRD pattern as depicted in FIG. 4; unit cell parameters substantially equal to the following at 180 K.:

| | |
|---|---|
| cell_length_a | 19.6428(6) Å |
| cell_length_b | 27.9098(8) Å |
| cell_length_c | 42.4271(12) Å |
| cell_angle_alpha | 90° |
| cell_angle_beta | 90° |
| cell_angle_gamma | 90° |
| cell_volume | 23259.7(12) Å$^3$ |
| symmetry_cell_setting | 'orthorhombic' |
| symmetry_space_group_name | P2$_1$2$_1$2$_1$ | and combinations of these data. Alternatively, crystalline form C of Voclosporin can be characterized by a PXRD pattern having peaks at 6.3, 7.0, 8.3, 12.2 and 14.1 degrees 2-theta #0.2 degrees 2-theta.

Further alternatively, crystalline form C of Voclosporin can be characterized by unit cell parameters substantially equal to the following at 180 K.:

| | |
|---|---|
| cell_length_a | 19.6428(6) Å |
| cell_length_b | 27.9098(8) Å |
| cell_length_c | 42.4271(12) Å |
| cell_angle_alpha | 90° |
| cell_angle_beta | 90° |
| cell_angle_gamma | 90° |
| cell_volume | 23259.7(12) Å$^3$ |
| symmetry_cell_setting | 'orthorhombic' |
| symmetry_space_group_name | P2$_1$2$_1$2$_1$ |

Crystalline form C of Voclosporin may be further characterized by the PXRD pattern having peaks at 6.3, 7.0, 8.3, 12.2 and 14.1 degrees 2-theta±0.2 degrees 2-theta, and also having one, two, three, four or five additional peaks at 8.9, 10.0, 10.4, 11.4 and 18.1 degrees 2-theta±0.2 degrees 2-theta.

Crystalline form C of Voclosporin may be characterized by each of the above characteristics alone or by all possible combinations, e.g., by PXRD pattern having peaks at 6.3, 7.0, 8.3, 12.2 and 14.1 degrees 2-theta±0.2 degrees 2-theta and a PXRD pattern as depicted in FIG. 4

Crystalline form C of Voclosporin may be alternatively or additionally characterized by the PXRD pattern having peaks at 6.3, 7.0, 8.3, 8.9, 10.0, 10.4, 11.4, 12.2, 14.1 and 18.1 degrees 2-theta±0.2 degrees 2-theta.

The present disclosure also provides the use of the solid state forms of Voclosporin and salts thereof, for preparing other solid state forms of Voclosporin, Voclosporin salts and solid state forms thereof.

A process for increasing the ratio of Voclosporin in a mixture comprising Voclosporin and cis-Voclosporin, comprising silica gel column chromatography using a mobile phase comprising methylisobutylketone and toluene, wherein the ratio of methylisobutylketone to toluene is from: about 25:75 to about 45:55, about 30:70 to about 45:55, or about 38:62. The fractions may be combined and the solvents removed to obtain the product.

The process may further comprise crystallising the product obtained after chromatography from a mixture of acetone and water, preferably in a volume ratio of from: about 1:1 to about 1:8, about 1:1 to about 1:5, about 1:1 to about 1:3 and more preferably about 1:2.

The crystallising preferably comprises dissolving the product in acetone, and adding water. Preferably, the mixture is cooled to about 0° C. to about 10° C., about 2° C. to about 8° C., or about 3° C. to about 6° C., and preferably about 4° C. The cooling may be carried out for about 0.5 hours to about 8 hours, about 1 to about 5 hours, about 1 to about 2 hours, or about 2 hours. The product may be isolated by any suitable procedure, preferably by filtration and dried. The drying may be carried out at a temperature of 20° C. to about 60° C., about 30° C. to about 50° C. or about 40° C. Preferably, the drying may be carried out under reduced pressure, preferably about 20 mbar to about 200 mbar, about 30 mbar to about 100 mbar, about 40 mbar to about 60 mbar, particularly about 50 mbar. The drying may be carried out for a period of time suitable to remove substantially all solvents, preferably for about 4 hours to about 48 hours, about 8 hours to about 24 hours, about 10 hours to about 15 hours, or about 12 hours. The product from the above process typically has a substantially reduced cis-Voclosporin content, preferably no more than about 1%, no more than 0.8%, no more than 0.5%, no more than 0.4%, or no more than 0.2%, and preferably no more than 0.1%, preferably as measured by HPLC (area percent). The product may be substantially free of cis-Voclosporin.

The above process may further comprise combining the Voclosporin with a pharmaceutically acceptable excipient to prepare a pharmaceutical composition.

The present disclosure further encompasses processes for preparing solid state forms of Voclosporin according to the present disclosure or other solid state forms thereof. The process comprises preparing the solid state form of the present disclosure, and converting it to other solid state form of Voclosporin. In another embodiment the present disclosure encompasses the above described solid state forms of Voclosporin and salts thereof, for use in the preparation of pharmaceutical compositions and/or formulations, preferably for the treatment of Lupus nephritis.

In another embodiment the present disclosure encompasses the use of the above described solid state forms of Voclosporin and salts thereof, or combinations thereof, for the preparation of pharmaceutical compositions and/or formulations, preferably oral formulations, e.g. tablets or capsules.

The present disclosure further provides pharmaceutical compositions comprising the solid state forms of Voclosporin and salts thereof, or combinations thereof, according to the present disclosure.

In yet another embodiment, the present disclosure encompasses pharmaceutical formulations comprising at least one of the above described solid state forms of Voclosporin and salts thereof or combinations thereof, and at least one pharmaceutically acceptable excipient.

Pharmaceutical formulations of the present disclosure contain any one or a combination of the solid state forms of Voclosporin of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, the active ingredient and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiment the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, n embodiments a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, which causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Voclosporin may be formulated for administration to a mammal, in embodiments a human. Voclosporin can be formulated, for example, as a viscous liquid solution or suspension, in embodiments a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The present disclosure encompasses a process to prepare said formulations of

Voclosporin by combining at least one of the above solid state forms and at least one pharmaceutically acceptable excipient.

The solid state forms as defined herein, as well as the pharmaceutical compositions or formulations of Voclosporin can be used as medicaments, in embodiments for the treatment of Lupus nephritis.

The present disclosure also provides a method of treating Lupus nephritis, comprising administering a therapeutically effective amount of the solid state form of Voclosporin of the present disclosure, or at least one of the above pharmaceutical compositions or formulations, to a subject suffering from Lupus nephritis or otherwise in need of the treatment.

The present disclosure also provides the use of the solid state forms of Voclosporin of the present disclosure, or at least one of the above pharmaceutical compositions or formulations for the manufacture of a medicament for treating Lupus nephritis.

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Analytical Methods

Powder X-Ray Diffraction Pattern ("PXRD") Method:

Powder X-ray Diffraction was performed on an X-Ray powder diffractometer PanAlytical X'pert Pro; CuKα radiation (λ=1.54187 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement Parameters:

| Scan range | 3-40 degrees 2-theta |
| --- | --- |
| Scan mode | continuous |
| Step size | 0.0167 degrees |
| Step size | 42 s |
| Sample spin | 60 rpm |
| Sample holder | zero background silicon plate |

X-Ray Crystal Structure Determination

Data were collected on a Rigaku Xcalibur PX system equipped with Onyx CCD detector and a Cu Kα sealed tube (λ=1.54178 Å) with an Enhanced monochromator using combined q and ω scans at 180 K. Data collection: CrysAlisPro CCD (Oxford Diffraction, 2002); cell refinement: CrysAlisPro RED; data reduction: CrysAlisPro RED; program used to solve structure: Sir2014 (Burla et al., 2015); program used to refine structure and absolute configuration analysis: CRYSTALS (Betteridge et al., 2003); molecular graphics: Mercury, DS ViewerPro. Data export (Appendix 1) and void calculation was done by Platon (Spek, 2003).

FTIR Spectroscopy Method:

FTIR transmission spectrum was recorded on Nicolet 380 spectrometer, equipped with KBR beam splitter and DTGS KBr detector.

Instrument Parameters:

| Spectral range: | 4000-400 cm$^{-1}$ |
| --- | --- |
| Resolution: | 4.0 cm$^{-1}$ |
| Number of scans: | 128 |
| Sample gain: | 1 |
| Optical velocity: | 0.6329 |
| Aperture: | 100 |

$^{13}$C Solid State NMR Method:

$^{13}$C CP/MAS NMR spectra were measured at 125 MHz using Bruker Avance III 500 WB/US NMR spectrometer (Karlsruhe, Germany, 2003) at magic angle spinning (MAS) frequency $\omega_r/2\pi=11$ kHz. In all cases finely powdered samples were placed into 4-mm ZrO$_2$ rotors and the standard "cpmas" pulseprogram was used. During acquisition of the data the high-power dipolar decoupling "TPPM" (two-pulse phase-modulated) was applied. The flip-pulse length was 4.8 μs. Applied nutation frequency of B1(1H) field was $\omega_1/2\pi=89.3$ kHz. Nutation frequency of $B_1(^{13}C)$ and $B_1(^1H)$ fields during cross-polarization was $\omega_1/2\pi=62.5$ kHz. The number of scans was 2048. Taking into account frictional heating of the samples during fast rotation all NMR experiments were performed at 293 K (precise temperature calibration was performed).

The NMR spectrometer was completely calibrated and all experimental parameters were carefully optimized prior the investigation of samples. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time).

HPLC Method:

Method Description

Column: Zorbax SB C18, 1.8 μm, 100×2.1 mm

Mobile phase: A: 38 ACN: 7 TBME: 55 voda: 0.02 H$_3$PO$_4$ (V/V/V/V)

B: 70 ACN: 7 TBME: 23 voda: 0.02 H$_3$PO$_4$ (V/V/V/V)

Flow rate: 0.5 mL/min

Gradient

| Time [min] | A [%] | B [%] |
| --- | --- | --- |
| 1 | 0.0 | 100.0 | 0.0 |
| 2 | 26.0 | 40.0 | 60.0 |
| 3 | 26.1 | 100.0 | 0.0 |
| 4 | 29.0 | 100.0 | 0.0 |

Analysis time: 26 minutes+3 minutes equilibration

Injection volume: 3.0 μL

Column temperature: 90° C.

Diluent: Ethanol

Detection: UV, 210 nm

EXAMPLES

The starting material Voclosporin crude may be obtained according to U.S. Pat. No. 6,998,385 Unless otherwise indicated, the purity is determined by HPLC (area percent). The crude product contained according to HPLC analysis 42.6% trans-Voclosporin (further only Voclosporin), 40.2% cis-Voclosporin and 2.9% Cyclosporin A. The crude Voclosporin was purified by column chromatography on silica gel using a mixture of toluene and acetone 82:18 (v/v) as mobile phase. The fractions were monitored by HPLC. The appropriate fractions were joined and evaporated, obtaining purified Voclosporin as a white foam. According to HPLC analysis it contained 85.7% Voclosporin, 3.6% cis-Voclosporin and 2.6% Cyclosporin A (further only purified Voclosporin).

The Voclosporin crude (containing about 42.6% of Voclosporin) was used for further optimization of the chromatographic separation of cis-Voclosporin and Voclosporin and the effort resulted in improved process for chromatographic separation which includes purification by column chromatography on silica gel using a mixture of toluene and methylisobutylketone 38:62 as mobile phase. The fractions were monitored by HPLC. The appropriate fractions were joined and evaporated to a dry residue, weighing 31.0 grams. This residue was not analyzed. The material was dissolved in 25 ml of acetone and then 50 ml of water was added and the solution was let to crystallize for 2 hours in the refrigerator. Then the crystalline product was separated by filtration and dried in vacuum dryer (40° C., 50 mbar, 12 hours), obtaining 29.6 g of dry product containing 90.6% of Voclosporin, 0.4% cis-Voclosporin and 3.7% Cyclosporin A (further mentioned as final Voclosporin).

Example 1: Preparation of Voclosporin Form A 4.1 grams of Purified Voclosporin was dissolved in acetone and the solution was evaporated to 8.0 grams and the concentrate was diluted by 6 ml of water. The solution was let to crystallize in refrigerator at about 2° C. for 12 hours. The crystalline product was filtered off, washed by a mixture of acetone and water 1:1 (v/v) and dried on open air obtaining 2.6 grams of crystalline product Form A. Voclosporin form A was confirmed by PXRD as presented in FIG. 1.

Example 2: Preparation of Voclosporin Form B 1.0 gram of Purified Voclosporin was dissolved in a mixture of 1.5 ml acetone and 3.0 ml n-hexane. The solution was let to crystallize in refrigerator at about 2° C. for 12 hours. The crystalline product was filtered off, washed by a mixture of acetone and hexane 1:2 (v/v) and dried on open air obtaining 0.5 grams of crystalline product Form B. Voclosporin form B was confirmed by PXRD as presented in FIG. 2.

Example 3: Preparation of Amorphous Voclosporin 2.0 grams of Purified Voclosporin was dissolved in 40 ml of hot cyclohexane and the solution was stirred for 12 hours at room temperature. Then the crystalline product was filtered off and washed with 5 ml of cyclohexane and dried on open air, obtaining 1.3 grams of amorphous powder. Amorphous Voclosporin was confirmed by PXRD as presented in FIG. 3

Example 4: Preparation of Voclosporin Form C

Final Voclosporin (2 grams) was dissolved in acetonitrile (20 ml) at 50° C., water (6 ml) was added with stirring, and the clear solution was allowed to crystallize 5 days at 20° C. Colorless needle crystals were directly mounted to the goniometer head in order to define the crystal structure. Voclosporin form C was confirmed by X-ray crystal structure determination.

Example 5: Preparation of Voclosporin Form B

Final Voclosporin (0.1 grams) was dissolved in ethanol (1 ml) at RT, water (0.5 ml) was added with stirring, and solution was allowed to crystallize at about 5° C. Colorless crystals were formed within 5 days, were recovered by filtration, and dried on air. Voclosporin form B was confirmed by PXRD.

Example 6: Preparation of Voclosporin Form B

Final Voclosporin (5 grams) was dissolved in acetone (20 ml) at RT and volume of acetone was then reduced to one half on vacuum evaporator. Water (6 ml) was added with stirring and solution was allowed to crystallize at about 5° C. Colorless crystals were formed within 2 days, were recovered by filtration, and dried on air. Voclosporin form B has been confirmed by PXRD.

The invention claimed is:

1. A crystalline form of Voclosporin, characterized by data selected from one or more of the following:
   (a) a PXRD pattern having peaks at 6.3, 7.0, 8.3, 12.2 and 14.1 degrees 2-theta±0.2 degrees 2-theta;
   (b) a PXRD pattern substantially as depicted in FIG. 4;
   (c) unit cell parameters at 180 K substantially as follows:

| | |
|---|---|
| cell length a | 19.6428(6) Å |
| cell length b | 27.9098(8) Å |
| cell length c | 42.4271(12) Å |
| cell angle alpha | 90° |
| cell angle beta | 90° |
| cell angle gamma | 90° |
| cell volume | 23259.7(12) Å$^3$ |
| symmetry cell setting | orthorhombic |
| symmetry space group name | $P2_12_12_1$; and |

(d) combinations of any two or more of (a), (b) and (c).

2. The crystalline form of Voclosporin according to claim 1, characterized by a PXRD pattern having peaks at 6.3, 7.0, 8.3, 12.2 and 14.1 degrees 2-theta±0.2 degrees 2-theta, and also having any one, two, three, four or five additional peaks at 8.9, 10.0, 10.4, 11.4 and 18.1 degrees 2-theta±0.2 degrees 2-theta.

3. The crystalline form of Voclosporin according to claim 1, containing: 1% or less, 0.8% or less, 0.5% or less, 0.4% or less, 0.2% or less, or 0.1% or less of cis-Voclosporin.

4. The crystalline form of Voclosporin according to claim 1, containing 5% or less, 4% or less, 3% or less, 2% or less, or 1% or less of Cyclosporin A.

5. The crystalline form of Voclosporin according to claim 1, containing: 0.5% or less of cis-Voclosporin and 4% or less of Cyclosporin A, 0.4% or less of cis-Voclosporin and 3% or less or Cyclosporin A, 0.3% or less of cis-Voclosporin and 2% or less of Cyclosporin A, or 0.2% or less of cis-Voclosporin and 2% or less of Cyclosporin A.

6. The crystalline form of Voclosporin according to claim 1, containing: 20% or less, 10% or less, 5% or less, 2% or less, 1% or less, 0.5% or less, or about 0% of any other solid state forms of Voclosporin.

7. A pharmaceutical composition comprising the crystalline form of Voclosporin according to claim 1.

8. A pharmaceutical formulation comprising the crystalline form of Voclosporin according to claim 1 and at least one pharmaceutically acceptable excipient.

9. A medicament comprising the crystalline form of Voclosporin according to claim 1.

* * * * *